United States Patent [19]

Pawluk

[11] Patent Number: 4,955,886
[45] Date of Patent: Sep. 11, 1990

[54] DUAL-TAPER, ASYMMETRIC HOLE PLACEMENT IN RECONSTRUCTION AND FRACTURE PLATES

[75] Inventor: Robert J. Pawluk, Montvale, N.J.

[73] Assignee: The Trustees of Columbia University in the City of New York, New York, N.Y.

[21] Appl. No.: 176,651

[22] Filed: Apr. 1, 1988

[51] Int. Cl.⁵ .............................................. A61F 5/04
[52] U.S. Cl. ................................................ 606/69
[58] Field of Search ............. 128/92 D, 92 R, 92 YP, 128/92 YF, 92 YK, 92 YV; 606/69, 88

[56] References Cited

U.S. PATENT DOCUMENTS

| | | | |
|---|---|---|---|
| 2,580,821 | 1/1952 | Nicola | 128/92 |
| 4,119,092 | 10/1978 | Gil | 128/92 YP |
| 4,219,015 | 8/1980 | Steinemann | 128/92 YP |
| 4,297,993 | 11/1981 | Härle | 128/92 YP |
| 4,403,607 | 9/1983 | Woo et al. | 128/92 YP |
| 4,429,690 | 2/1984 | Angelino-Pievani | 128/92 YP |
| 4,488,543 | 12/1984 | Tornier | 128/92 BB |
| 4,503,848 | 3/1985 | Caspar et al. | 128/92 D |
| 4,573,458 | 3/1986 | Lower | 128/92 YP |
| 4,683,878 | 8/1987 | Carter | 128/92 YP |
| 4,773,406 | 9/1988 | Spector et al. | 128/92 YP |

FOREIGN PATENT DOCUMENTS

| | | | |
|---|---|---|---|
| 0207884 | 1/1987 | European Pat. Off. | 128/92 YP |
| 2367479 | 5/1978 | France | 128/92 YP |

Primary Examiner—Robert A. Hafer
Assistant Examiner—Charles H. Sam
Attorney, Agent, or Firm—John P. White

[57] ABSTRACT

The invention relates to a reconstruction or fracture plate for bridging a discontinuity in a patient's long bone, such as a femur and has a central portion for placement over the bone discontinuity, a first end portion having a dual-tapered width and thickness profile having a first plurality of screw holes and a second end portion defining a second plurality of screw holes. The first and second plurality of screw holes each have asymmetrically arrayed centerlines relative to plate longitudinal and transversal axes and the screw holes may have asymetrically arrayed centerlines relative to each other. Both the first and second end portions may have dual-tapered profiles.

9 Claims, 8 Drawing Sheets

DUAL-TAPER, ASYMMETRIC HOLE PLACEMENT IN RECONSTRUCTION AND FRACTURE PLATES

BACKGROUND OF THE INVENTION

This invention relates generally to internal osteosynthesis plates for fracture or reconstructive repair of long bones in patients, such as the humerus, radius, ulna, tibia and femur. A common principle in long-bone fracture management is interfragmentary contact and stabilization until sufficient osseous healing occurs to mobilize the fracture. During this period, an adequate healing response relies on the combination of bone-to-bone contact and plate fixation to obtain the optimum load sharing distribution across the reparative site. However, in contrast to fracture repair, there are clinical situations requiring major long-bone reconstruction; as in leg-length inequality, major reconstruction after trauma, or following radical tumor resection, wherein cortical bone-to-bone contact is initially absent at the reparative site and must be repaired by bone grafts. These latter bone graft cases, by their very nature, preclude the important biomechanical advantage of early load sharing offered by cortical bone contact. In these instances, any load transfer must be through the plate and associated plate screws until adequate osseous consolidation allows for functional load sharing between bone segments and the internal fixation device.

In fracture fixation or reconstructive procedures, a bony discontinuity, be it a fracture with or without adequate reduction, or a bone gap, as in reconstructive procedures, must be suitably stabilized and provide sufficient load transfer. Although it has been widely reported that inadequate anatomic reduction during fracture fixation can result in excessively high plate stresses, which can lead to premature failure, little is known about the loads being simultaneously transferred through the individual plate screws. Furthermore, if bone-to-bone contact is not achieved in fracture reduction, or can not be achieved as in long-bone reconstruction, then even greater load demands must be placed upon individual plate screws.

During the past ten years, there has been a substantial increase in long-bone reconstruction surgery employing autogenous cancellous bone grafts where bone-to-bone contact can not be initially achieved. Because these bone gaps average five centimeters, osseous healing requires many months to consolidate sufficiently prior to full weight-bearing, thus imposing high, long-term loading demands upon the plate and screw fixation systems now in use. Further complicating an uneventful rehabilitation of these patients is the desire and need for early controlled ambulation, to expedite osseous healing, which results in additional loading of the plate-screw fixation system.

The standard leg-lengthening plate, currently in surgical use today, is essentially a broad or narrow fracture plate whose mid-section is simply elongated and devoid of screw holes in order to bridge a large bone graft site. Since a fracture plate is generally intended for use with cortical bone-to-bone contact, its design is unsuitable for use in surgical situations where bone contact is initially absent or unstable, as in reconstructive surgery involving large gap bone grafts. Therefore, a fracture plate with a simple elongated mid-section can not be relied upon to support early ambulation or unusual intermittent higher loads, since its inherent total stiffness, associated with asymmetric femoral loading, transfers significantly greater non-uniform bending strains to the plate screws. In the presence of asymmetric long-bone bending, excessive screw bending strains are produced and result in a high percentage of screw failures in these fixation regions, with subsequent loss of plate fixation. Analysis of radiographs have demonstrated that the sequence of femoral screw failure generally starts at the most proximal plate screw (i.e., the screw closest to the patient's pelvis at the plate tip) and proceeds distally towards the plate mid-section. Scanning electron microscopy studies of failed screw surfaces have been conducted and demonstrate that screw failure was predominantly the result of bending fatigue rather than shear failure.

The highly asymmetrical failure pattern of these plate screws—almost all proximal to the plate mid-section, in association with individual screws predominantly failing in bending—gave rise to the theory that asymmetrical femoral bending, during loading, was the cause of these clinical implant failures. Furthermore, any long-bone subjected to asymmetric bending during loading would demonstrate non-uniform screw strains if the fracture or fixation plate used is symmetrical in shape on either side of the reparative site. The significance of this invention is that the plate fixation design is more appropriately matched to the loading requirements of individual long-bones as opposed to plates designed to fit the anatomical contours of a bone or the site of reparative fixation.

To investigate further the mechanism of clinical failure, a single-stance anatomic model was employed by me to simulate the fixation mechanics of the then-current surgical leg-lengthening procedure. This analysis demonstrated that asymmetric loading of the femur could result in abnormally high screw bending strains leading to the screw bending fatigue seen clinically. Based on these studies, the operative procedure was modified by surgically positioning the conventional leg-lengthening plate as posteriorly as possible to counteract the large lateral bending moments produced along the proximal femoral shaft. To reduce further excessive bending strain levels on a per-screw basis, ten-hole plates (five screws on each side of the bone gap) were substituted for the normally used eight-hole plates (four screws on each side of the bone gap). Although the posteriorly-positioned, ten-hole plate did reduce proximal screw failures, its surgical placement was not easily accomplished, nor could it serve as a permanent solution in reducing excessive strains on the proximal plate screws. However, plate repositioning did reduce screw failures, thus providing clinical confirmation that excessively high bending loads were being applied to the proximal plate screws.

These research studies and associated clinical results clearly indicated the need to understand better the basic interrelationships involving the transfer of screw loads between plate and bone during osseous healing, both for long-term reconstruction and fracture repair. In fact, one may take the position that a dichotomy exists in observing two grossly different modes of implant failure for two relatively similar fixation conditions. For example, implant failure during delayed or non-unions of poorly reduced midshaft femoral fractures result primarily in plate failure, while in femoral reconstruction cases, broken screws are the primary cause of failure.

My studies have demonstrated that there are substantial differences in the transfer of screw loads during fracture repair as opposed to long-bone reconstruction, thus providing a unique insight into the mechanisms of plate fixation. Furthermore, these studies provided the basis for the development by me of the dual taper, asymmetric hole placement in reconstruction and fracture plates of the present invention.

It is an object of the present invention to create a reconstruction or fracture plate suitable for use in large-gap, long bone grafts, that is less susceptible to anchoring screw and plate failure than previously known reconstruction or fracture long bone plates, that eliminates medical complications caused by failure, such as potential loss of the patient's leg length; increased medical risks from delayed bone union; increased hospitalization and costs associated therewith; and additional surgery necessary to salvage the plate failure.

More particularly, it is an object of the present invention to create a reconstruction or fracture plate, having varying flexibility along the plate and an asymmetrical array of screw holes for receipt of anchoring screws, that distributes more equalized loads to each screw than previously known plates, while secondarily improving load transfer at the reparative site and reducing stress shielding.

SUMMARY OF THE INVENTION

These objects have been attained with the reconstruction or fracture long bone plates as described and claimed in the present invention in which their unique flexibility and asymmetrical screw hole placement reduce the likelihood of screw or plate fatigue.

The present invention relates to a reconstruction or fracture plate for bridging a discontinuity in a long bone of a patient comprising a longitudinal axis for placement generally in alignment with a long axis of the long bone; a transversal axis perpendicular to the longitudinal axis; a central portion for placement over the bone discontinuity; a first end portion for abutting placement against the long bone on one side of the bone discontinuity, the first end portion having a dual-tapered width and thickness profile for varying plate cross section along the longitudinal axis away from the central portion and the first end portion defining a first plurality of screw holes; and a second end portion for abutting placement against the long bone on a second side of the bone discontinuity, defining a second plurality of screw holes; the first and second plurality of screw holes each having asymmetrically arrayed center lines relative to the plate longitudinal and transversal axes.

The present invention also relates to a reconstruction or fracture plate for bridging a discontinuity in a long bone of a patient, comprising a longitudinal axis for placement generally in alignment with a long axis of the long bone; a transversal axis perpendicular to the longitudinal axis; a central portion for placement over the bone discontinuity; a first end portion for abutting placement against the long bone on one side of the bone discontinuity, the first end portion having dual-tapered width and thickness profile for varying the plate cross section along the longitudinal axis away from the central portion and defining six (6) screw holes; and a second end portion for abutting placement against the long bone on a second side of the bone discontinuity, defining four (4) screw holes; each of the screw holes having asymmetrically arrayed centerlines relative to the plate longitudinal and transversal axes.

BRIEF DESCRIPTION OF THE FIGURES

FIG. 9 is a graph showing screw bending strain distributions in a plate of the present invention when installed on intact bones, as well as bone gaps from 2 mm to 40 mm.

DETAILED DESCRIPTION OF THE INVENTION

The present invention includes a reconstruction or fracture plate for bridging a discontinuity in a long bone of a patient comprising a longitudinal axis for placement generally in alignment with a long axis of the long bone and a transversal axis perpendicular to the longitudinal axis. The plate also comprises a central portion for placement over the bone discontinuity and a first end portion for abutting placement against the long bone on one side of the bone discontinuity. The first end portion has a dual-tapered width and thickness profile for varying plate cross section along the longitudinal axis away from the central portion. The first end portion also defines a first plurality of screw holes. The plate further comprises a second end portion for abutting placement against the long bone on a second side of the bone discontinuity, which defines a second plurality of screw holes. The first and second plurality of screw holes each have asymmetrically arrayed center lines relative to the plate longitudinal and transversal axes.

The reconstruction or fracture plate of the present invention may have a first end portion with a greater number of screw holes than the second end portion.

Desirably, the first end portion has six (6) screw holes and the second end portion has four (4) screw holes.

In another embodiment of the present invention, the reconstruction or fracture plate second end portion also has a dual-tapered width and thickness profile for varying plate cross section along the longitudinal axis away from the central portion. In this other embodiment, the first end portion may have six (6) screw holes and the second end portion may have four (4) screw holes.

In the reconstruction or fracture plate of the present invention, either the first or second plurality of screw holes or both may have asymmetrically arrayed centerline spacing relative to each other.

In some embodiments, the reconstruction or fracture plate of the present invention may be used for bridging a discontinuity in a long bone of a patient and comprises a longitudinal axis for placement generally in alignment with a long axis of the long bone and a transversal axis perpendicular to the longitudinal axis. Such a plate also has a central portion for placement over the bone discontinuity; a first end portion for abutting placement against the long bone on one side of the bone discontinuity, with the first end portion having dual-tapered width and thickness profile for varying the plate cross section along the longitudinal axis away from the central portion and defining six (6) screw holes. The plate also has a second end portion for abutting placement against the long bone on a second side of the bone discontinuity, defining four (4) screw holes. Each of the screw holes in the plate has asymmetrically arrayed centerlines relative to the plate longitudinal and transversal axes.

The following examples are illustrative of the reconstruction and fracture plates of the present invention, but they are in no way intended to restrict the scope of the claims hereto.

Referring generally to FIGS. 1-4, the reconstruction or fracture plates of the present invention have a longitudinal axis, L—L, for placement generally in alignment with a long axis of a long bone and a transversal axis T—T, that is perpendicular to the longitudinal axis. The plates may have a concave underside profile, for abutting the plates to the long bone outer surface. The plates are constructed of any material for use in orthopedic implants in patients, known to those skilled in the art. Examples of such materials include titanium, stainless steel or other metals; biocompatible, nonmetallic structural materials, including composite structural materials, or any combination thereof.

Figure 1:
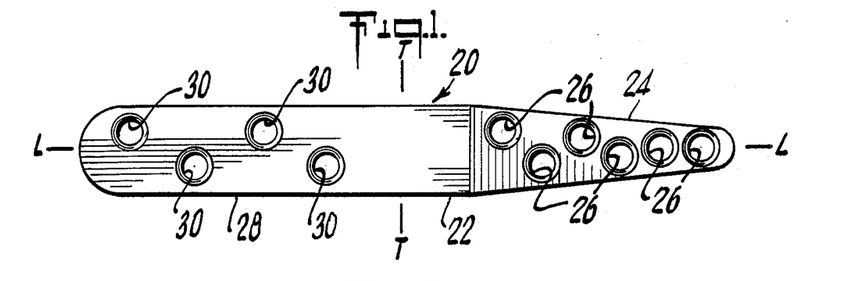
FIG. 1 is a plan view of one embodiment of a reconstruction or fracture plate of the present invention.
Figure 2:
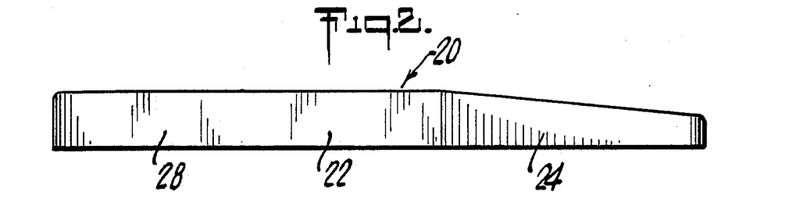
FIG. 2 is a elevational view of the reconstruction or fracture plate of FIG. 1.

FIGS. 1 and 2 show one embodiment of the reconstruction or fracture plate 20 of the present invention, having a central portion 22 for placement over a bone discontinuity, which may be a bone fracture site or a bone graft site. The central portion 20 length may be varied to accommodate different bone gap widths.

The plate 20 also has a first end portion 24 for abutting placement against the long bone on one side of the bone discontinuity having the greatest degree of bone bending as compared to the other side of the discontinuity. When the plate 20 is utilized in femoral fracture repair or lengthening procedures, the first end portion 24 is oriented on the proximal side of the bone discontinuity closest to the patient's pelvis. The first portion 24 has a dual-tapered width and thickness as shown in Figs. 1 and 2, so that the plate cross-sectional area is generally reduced along the longitudinal axis L—L from the central portion toward the right side of the figures.

Varying the plate cross-sectional area changes the plate 20 flexibility to compensate for asymmetrical, biomechanical loads exerted on each side of the patient's bone reparative site. As one skilled in the art can appreciate, it is a desirable design goal to transfer stresses and strains from the bone anchoring screws to the plate structure, in a manner so as to reduce screw failure.

Plate 20 first end 24 defines a plurality of screw holes 26 which have asymmetrically arrayed centerlines in both the longitudinal L—L and transversal T—T axes of the plate. I have found that such a centerline asymmetrical array along both axes provides the best distribution of stress and strain in each screw (26), in addition to reducing stresses and strains in those screws which are most distant from the plate central portion 22. In this embodiment, there are six (6) first end screw holes 26. The screw holes 26 have any configuration known to those skilled in the art that are suitable for receipt of attachment screws, such as cortical or cancellous screws.

The plate 20 has a second end portion 28 for abutting placement against the other side of the bone discontinuity. In femoral applications, the second end portion 28 is oriented on the side of the bone discontinuity closest to the patient's knee. The second end portion 28 of the embodiment shown in FIGS. 1 and 2 has a width and thickness profile identical to the central portion 22.

The second portion 28 defines a plurality screw holes 30. In this embodiment, shown in FIGS. 1 and 2, there are four (4) screw holes 30, which provides the best distribution of stress and strain in each screw. The second end screw holes 30 have an asymmetrical centerline array relative to both the longitudinal L—L and transversal T—T axes. The screw holes 30 have any configuration known to those skilled in the art that are suitable for receipt of attachment screws, such as cortical or cancellous screws.

Figure 3:
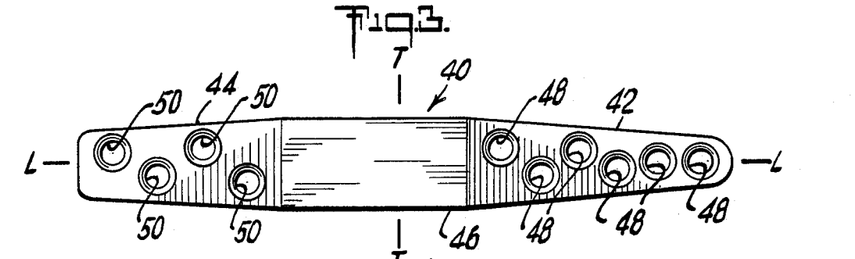
FIG. 3 is a plan view of another embodiment of a reconstruction or fracture plate of the present invention.
Figure 4:
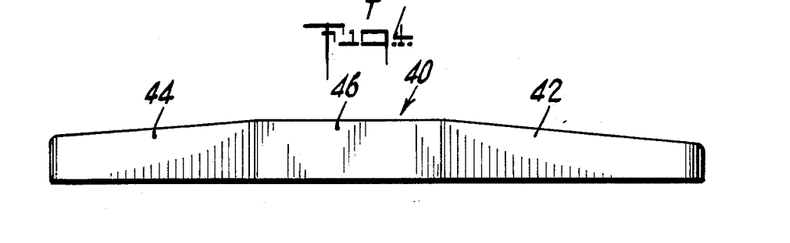
FIG. 4 is an elevational view of the reconstruction or fracture plate of FIG. 3.

FIGS. 3 and 4 show another embodiment of the present invention fracture or reconstruction plate 40, wherein both the first end 42 and second end 44 each have a dual-tapered width and thickness profiles, for varying plate flexure away from central portion 46. Each end 42 and 44 may have different tapered profiles. In this embodiment, the first end screw holes 48 and the second end screw holes 50 have asymmetrically arrayed centerlines along both the L—L and T—T axes. As shown, the first end 42 has six (6) screw holes and the second end 44 has four (4) screw holes.

The fracture or reconstruction plate of the present invention, as shown in FIGS. 1 and 2, incorporates a dual taper at one end of the plate combined with asymmetric screw hole placement, wherein six plate holes 26 are within the tapered first end 24 and four plate holes 30 are within the second end 28. By surgically orienting the plate's tapered end on the side of the bone discontinuity having the greater degree of bending, the plate offers less resistance to the bending, thereby reducing bending strains which act on the corresponding tapered end plate screws. In femoral repair applications, the addition of six proximal plate screw holes on the dual-tapered end increases, by fifty percent, the number of screw load transfer points over the known, conventional eight-hole plate, with four holes on each side of the bone gap, while still retaining adequate distal screw fixation and the original length of the known plates. The combined design of plate taper and asymmetrical screw hole placement provides substantial reductions in proximal screw bending strains, so that lateral positioning of the plate along the femur can be achieved for easier and less traumatic surgical procedures.

While the plates shown in FIGS. 1–4 have generally straight tapered profiles, plates constructed in accordance with the principles of the present invention may have any variable width and thickness profile that varies the plate cross section and thus plate flexure, in order to reduce plate resistance to functional loading of the long bone and reduce screw bending strains. Thus, the plate may be constructed with any desired generally concave, straight or convex tapered profile. The width and thickness tapers may be asymmetrical.

Figure 5:
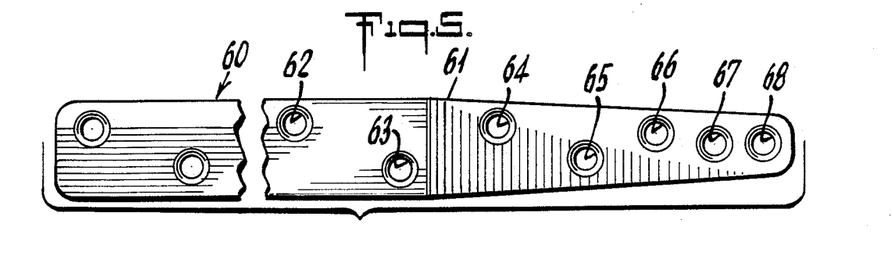
FIG. 5 is a plan view of another embodiment of a reconstruction or fracture plate of the present invention.

In the embodiment shown in FIG. 5, the plate 60 first end 61 asymmetrically varies the centerline spacing between adjacent screw holes 62–68, to reduce excessive strains on screws most prone to failure. For example, screw holes 62 and 63, which in use are oriented near the long bone reparative site, have a larger centerline spacing than screw holes 67 and 68, which are oriented farther from the reparative site. Asymmetry in screw hole centerline spacing, when combined with dual-tapered profile, allows even further reduction in plate 60 resistance to long bone functional loading than the embodiments shown in FIGS. 1–4.

The number of screws holes contained on the first and second end portions of the plate may also be varied to reduce excessive strains on screws most prone to failure. While the embodiments shown in FIGS. 1–4 have six (6) first end screws and four (4) second end screws, other screw combinations may be used, such as for example, seven (7) first end screws, shown in FIG. 5, and four (4) second end screws.

The preferred embodiments of the reconstruction and fracture plates of the present invention were created as a result of my experimental studies described below.

EXPERIMENTAL STUDIES

The present invention dual-taper plate of FIGS. 1 and 2 was evaluated and compared to known, conventional eight and ten-hole leg-lengthening plates, that do not have dual-tapered profiles with asymmetrically oriented screw arrays along the longitudinal and transversal axes, using strain-gage instrumented screws, plates and femora. This technique provided the means to monitor screw bending strain distributions from all plate screws under a variety of femoral loading conditions ranging from the intact femur to bone gaps up to 40 mm in width.

To determine the distribution of individual screw strains, as a function of load transfer between bone and plate, a strain measuring bone screw was developed. Strain gaged instrumented screws were fabricated from 70 mm malleolar screws by removing the head while retaining 29 mm of the original shank, 25 mm of which was re-threaded. The newly threaded section was designed to receive a substitute screw head in the form of an elongated 316 stainless steel nut whose underside geometry duplicated the original screw head shoulder. The remaining 4 mm of shank, between the standard cortical screw threads and the portion containing the screw head nut, provided a preselected region for instrumenting two uniaxial strain gages, which were aligned with the screw's long-axis and separated by 180 degrees. This method allowed for the controlled placement of each strain-gaged screw into predetermined femoral screw holes, so that the gage grid was approximately 1 mm above the periosteal bone surface, but still within the confines of the plate hole. The dual-taper plate of the present invention and eight- and ten-hole, prior art conventional leg-lengthening plates were instrumented mid-length with dual triaxial strain gages and then fitted over the appropriate number of strain-gaged screws and secured with the stainless steel nuts, torqued to 1 Nm.

To ensure gage function and provide baseline data for error analysis prior to the experimental study, strain gaged screws were calibrated in axial tension, bending and torque modes employing three separate testing devices. In addition, each plate was calibrated using specifically designed fixtures, thus affording controlled methods for comparing strain calibration curves prior to and after experimental application of plates and screws.

To simulate anatomic loading conditions for the plated femur and strain-gaged screws, a skeletal model was employed in the single-stance mode. Application of body weight is via the spine, while skeletal equilibrium is maintained through a load cell augmented abductor muscle mechanism. This anatomic model approach allows spinal loading between 10 and 70 kg, thus simulating femoral joint reaction forces within the range of partial to full weight bearing, while maintaining the clinical bending moments imposed upon the femur.

The experimental protocol first required strain measurements from medial and lateral femoral aspects prior to and after drilling the screw holes and then after tapping. Following these baseline control measurements, screw strain distributions were measured for the following experimental conditions: intact femur with strain-gaged screws and plate in place; bone-to-bone contract; followed by 2, 5 and 40 mm resection osteotomies. In selected cases, bone gap spacers of different stiffnesses were used to simulate various stages of osseous healing.

EXPERIMENTAL RESULTS

Conventional Eight-Hole Leg-Lengthening Plates

Figure 6:
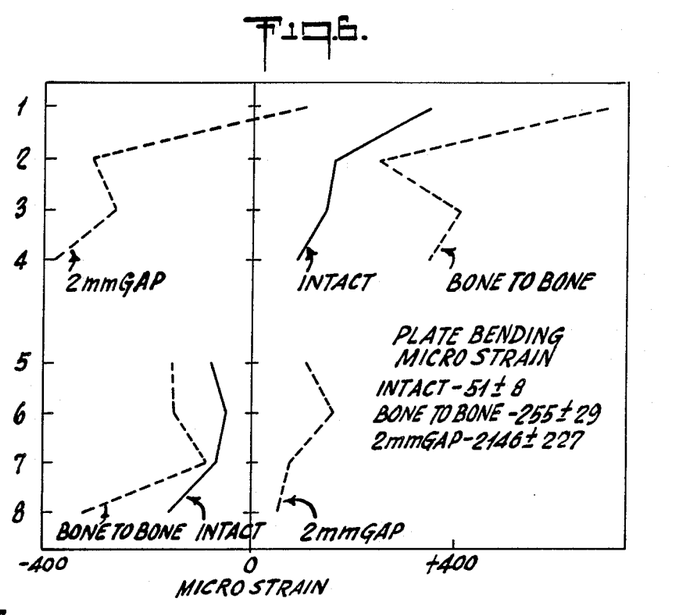
FIG. 6 is a graph showing screw bending strain distribution in a prior art 8-hole femoral plate.

The first set of data involve the testing of conventional eight-hole leg-lengthening plates in the anatomic single-stance mode. FIG. 6 demonstrates the effects on screw bending strain distributions, with respect to the superior aspect of the screws, for screw positions one (most proximal) through eight (most distal) as a function of intact, bone-to-bone contact, and 2 mm wide mid-shaft bone gap conditions. During these three conditions, plate bending strains were 51 ±8, 255 ±29, and 2,416 ±227, $\mu\epsilon$, respectively. However, even though there is a substantial reduction in the plate bending strain when a 2 mm bone gap is converted to the bone contact condition, a similar reduction in individual plate screw bending strains does not occur. Furthermore, it is only during the intact condition, considered as ideally "healed", that both plate and screw strain distributions attain their lowest bending strain values. Of clinical relevance, therefore, are the effects of bony discontinuities, such as bone-to-bone contact in fracture reduction, or the lack of bone contact such as in inadequate fracture reduction or during long-bone reconstruction, on screw strain magnitudes and their predominant bending directions, as exhibited by the proximal and distal screw groups.

Under the condition of bone-to-bone contact, net bending strains for the proximal and distal screw groups change by 240 ±33 and 87 ±16 $\mu\epsilon$ as compared to the "healed" condition. For the inadequately reduced fracture condition, employing a 2 mm gap, the average screw bending strains for the proximal and distal screw groups changed by 392 ±48 and 184 ±26 με, respectively as compared to the "healed" condition.

Similar changes in screw distributions over the idealized "healed" condition, represented by a plated intact femur, were also observed for 5 mm and 40 mm bone gap conditions. In addition, there was a net reversal in screw bending strain directions for both the proximal and distal screw groups when bone-to-bone contact was absent. For example, during bone-to-bone contact, all four distal screws were observed to be under compressive bending with respect to their superior surface, but undergo tensile bending if a 2 mm gap is present. The proximal screw group also demonstrated this change in bending direction in a converse fashion, starting first in tension and then changing to compressive bending with respect to the screw's superior surface. The only screw position which did not follow this sequence is the most proximal screw although its strain, in the tensile bending direction, did decrease appreciably.

Figures 7, 7A:
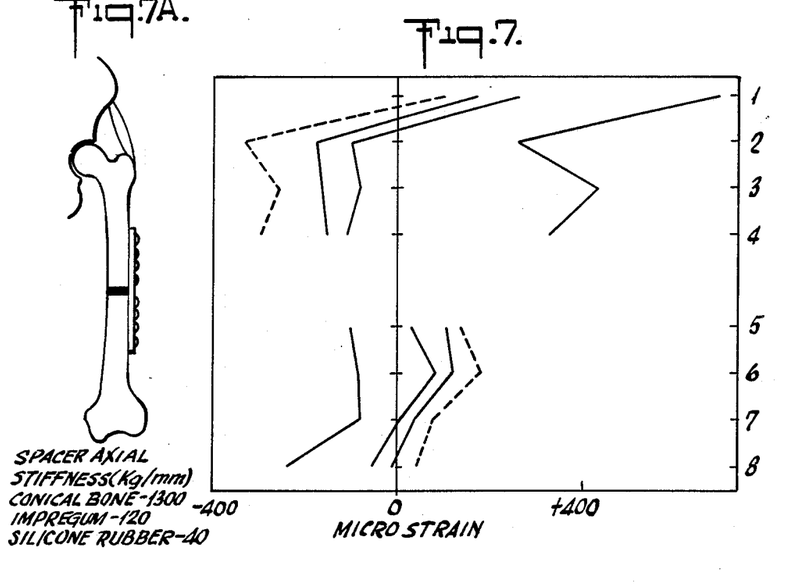
FIG. 7 is a graph showing screw bending strain distributions in a prior art 8-hole femoral plate, wherein axial spacers of differing stiffness have been inserted into a 5 mm bone gap.
FIG. 7A is a schematic diagram of the test apparatus used to measure the bone screw bending strain distribution shown in FIG. 7.

Of specific clinical importance is the effect of healing time or altering screw bending strain distributions as a function of osseous repair. To demonstrate these screw strain changes, selected stages of osseous healing were simulated, at the gap site, employing spacers with axial stiffnesses of 40 (graph line 105) and 120 (graph line 102) kg/mm as shown in FIGS. 7 and 7A. As femoral gap axial stiffness was increased, within a 5 mm bone gap, screw bending strains shifted away from the air gap condition (graph line 104) and toward the strain distribution levels obtained bone-to-bone contact. As the axial gap stiffness increases to that of headed bone (graph line 101), each of the plate screws would undergo a reversal in bending direction, excluding the most proximal screw. The same shift in screw bending strain distributions was also noted for 2 and 40 mm gap bone conditions. This phase of the study emphasized the important role long-term healing has on maintaining large screw bending strain levels, as opposed to much shorter healing periods associated with normal fracture repair.

Analysis of data derived from these plate studies resulted in the identification of four major patterns of screw bending strain distributions. As a group, these strain distribution patterns are significant not only for understanding the mechanism of load transfer during fracture fixation or long-bone reconstruction, but also in the analysis of implant failures. The four major screw strain distribution patterns are summarized below:

(1) As a function of load transfer between bone and plate, a non-linear bending strain distribution is exhibited by the eight plate screws, be it during bone-to-bone contact, gap conditions or when the bone is healed. Therefore, different load transferring functions can be attributed to each of the eight plate screws, depending upon the degree of healing.

(2) When a mid-shaft bone gap is present, the innermost plate screws, closest to the gap, are subjected to the greatest bending strains, whereas bone-to-bone contact or healed conditions produce the highest bending strains in the outer-most plate screws, farthest from the gap.

(3) During the bone-to-bone contact or for the healed condition, screws proximal to the plate mid-section exhibit tensile bending strains while distal screws simultaneously exhibit compressive bending strains.
( 4) During bone gap conditions, all screws, either proximal or distal to the plate midsection, will exhibit a reversal in bending direction (excluding the most proximal plate screw) relative to the bending direction observed for bone-to-bone contact or the healed condition.

All four screw bending strain patterns are characteristic of femoral plating, be it for fractures or reconstructive fixations, and can be typically observed when using either conventional, known prior art eight- or ten-hole plates.

Dual-Taper, Asymmetrically Arrayed Hole Reconstruction And Fracture Plates

For patients undergoing femoral leg-lengthening, the initial, previously known short-term surgical solution for reducing proximal screw failure involved the substitution of known ten-hole plates, positioned posteriorly in the patient, instead of eight-hole plates positioned laterally in the patient.

The concepts underlying the present invention of reconstruction and fracture plates were first to identify the mechanism of clinical screw failure and then to utilize these newly found strain distribution patterns to develop a new plate which significantly reduced changes in screw bending strain directions and maintained the lowest possible bending strains in the most proximal plate screws, thereby reducing premature screw failure.

To minimize proximal screw failures in femoral lengthening procedures, the plate shown in FIGS. 1 and 2 herein was designed, so that six plate holes were asymmetrically arrayed in the first end portion and oriented proximally to the gap and four plate holes were asymmetrically arrayed in the second end portion, oriented distally to the gap. This screw hole pattern provided a fifty percent increase in the number of screws available for distributing the proximal load transfer, compared with known eight-hole plates, while simultaneously limiting reverse bending of the most proximal screws.

In FIGS. 8–12, the notation "/" refers to the number of screw holes in the proximal portion of the studied plate versus the number of screw holes in the distal portion thereof. For example, a "6/4" plate has six proximal (first end) screw holes and 4 distal (second end) screw holes, respectively.

Figure 8:
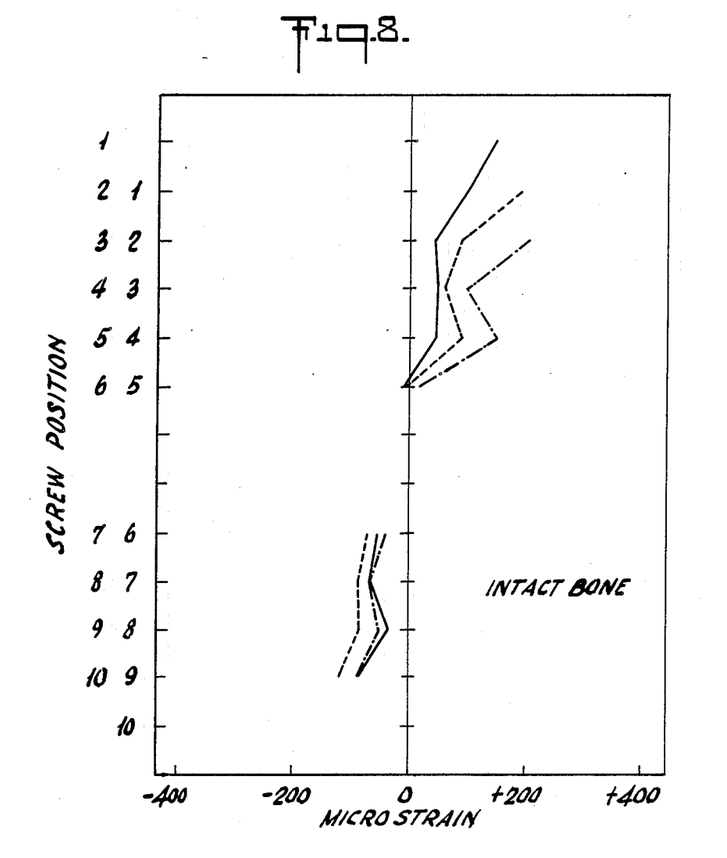
FIG. 8 is a graph comparing screw bending strain distributions in a non-tapered plate on an intact long bone, while using different quantities of proximal screws on the plate.

If the number of proximal plate screws are increased under the "healed" bone condition, then there will be a resultant decrease in the proximal screw bending strains. FIG. 8 demonstrates that a 6/4 non-tapered plate used with 6 proximal end screws (top graph line 107), rather than only 5 (top graph line 106) or 4 (top graph 105) proximal end screws, will result in a major reduction in proximal screw bending strains, while maintaining a relatively uniform strain level for the four distal screws.

FIG. 9 demonstrates the effect of bone gap widths (2 to 40 mm) on screw bending strain distributions for a 6/4 dual-tapered plate of the present invention. The graph line I denotes an intact bone. With increasing gap widths, the first three proximal screws have a reduction in bending strain, but do not reverse bend. The remaining three proximal screws (screws 4, 5, and 6) first exhibit a reduction in bending strain, then reverse their bending direction (tension to compression) and finally increase their bending strain. These changes in screw bending strain distributions are similar to those shown in FIG. 6; however, with a conventional 4/4 plate, three of four proximal screws are subjected to reverse bending, even for a bone gap as small as 2 mm.

Figure 10:
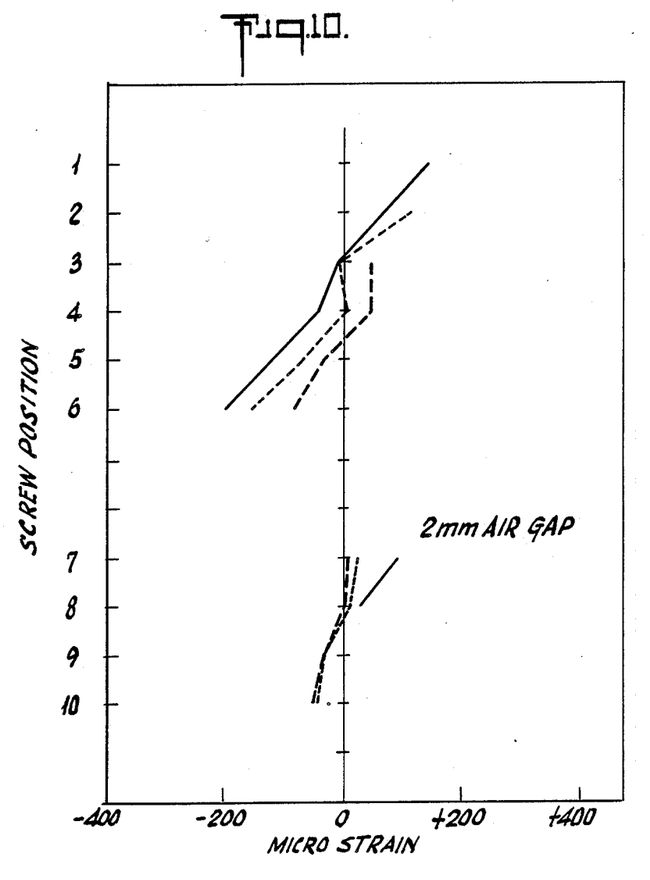
FIG. 10 is a graph comparing screw bending strains in a plate of the present invention using 6, 5 or 4 proximal screws, employing a 2 mm bone gap.
Figure 11:
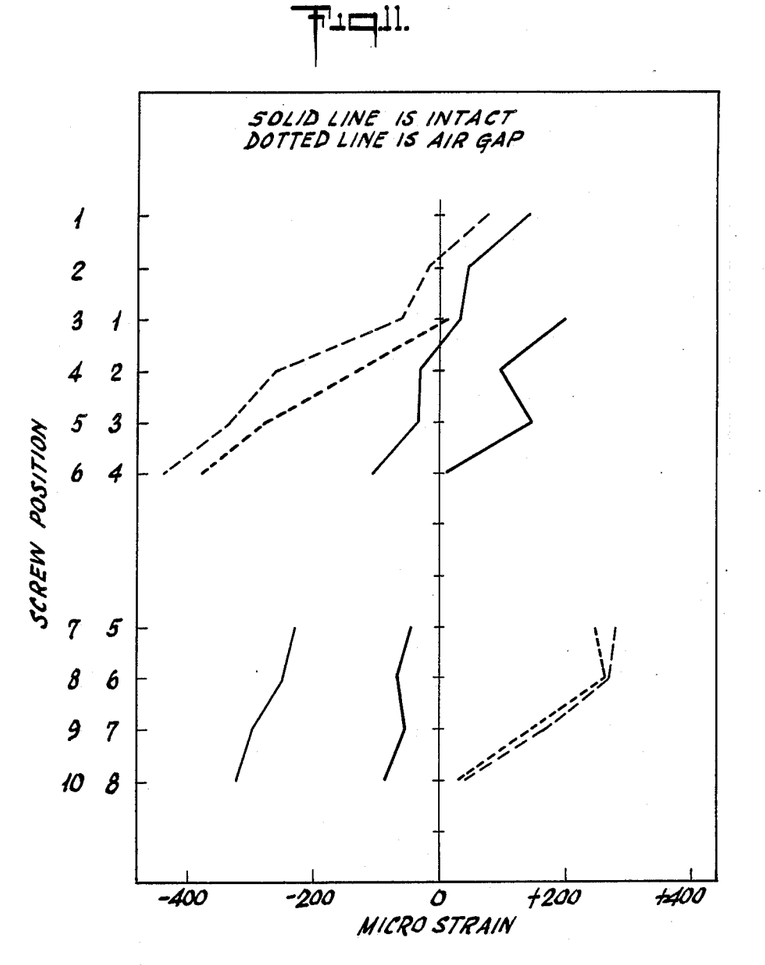
FIG. 11 is a graph comparing screw bending strains in a plate of the present invention with a prior art plate, when each is installed on an intact bone and on a bone with a 40 mm bone gap.
Figure 12:
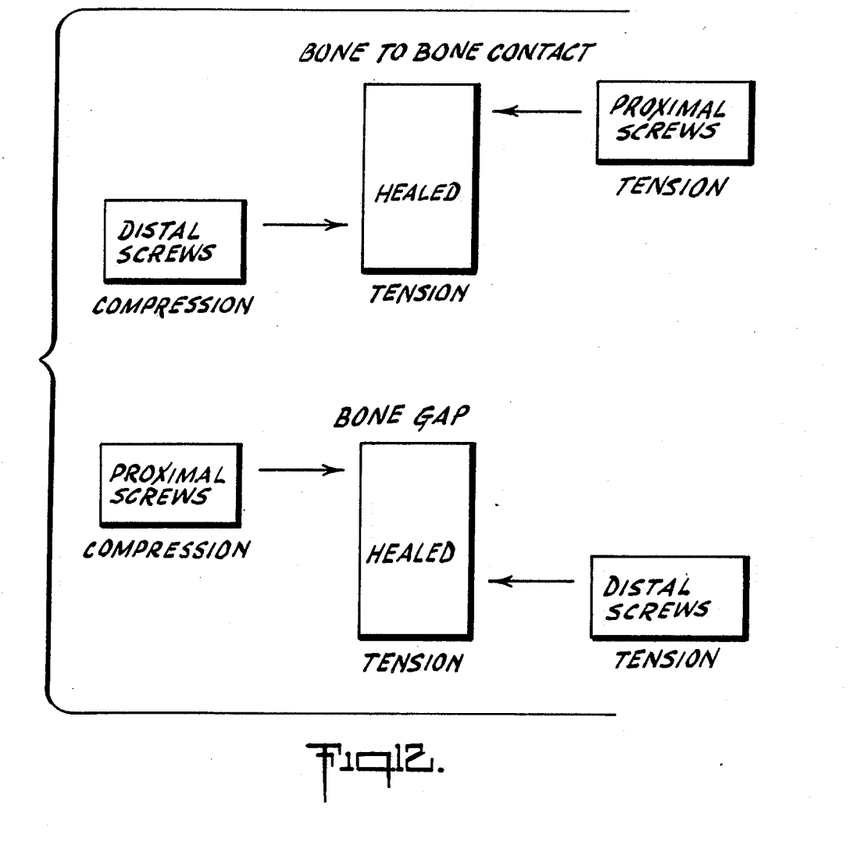
FIG. 12 is a diagram comparing screw bending strain distributions during fracture fixation with screw bending strain distributions during reconstruction or inadequate fracture reduction, when bone gaps are present.

The effect of a 2 mm bone gap on a 6/4 dual-tapered plate of the present invention, anchored with 4, 5 or 6 screws in the proximal end, is seen in FIG. 10. As, the number of proximal screws are increased from four (graph line 108) to five (graph line 109) to six ((graph line 110) the screw bending strain profiles, relative to the superior aspect of the screws, begin to shift from tensile to compressive bending. However, when six screws are used, the three most proximal screws of the 6/4 plate still maintain their original tensile bending direction, at a fairly uniform strain level. Several of the most proximal screw strain magnitudes for the 5/4 and 6/4 plate screw configurations are greater than that observed for the proximal 4/4 plate screws, with a bone gap width of only 2 mm. However, as the bone gap width increases to 40 mm, as seen in FIG. 11, the relationship between screw bending directions and strain magnitudes is clearly demonstrated by the lack of or minimal changes in the most proximal screw strains of the 6/4 dual-taper plate as compared to the conventional 4/4 leg-lengthening plate. FIG. 11 compares the screw bending strain distributions for a dual-taper 6/4 (graph line 112 and 114) and a conventional, prior art 4/4 leg-lengthening plate (graph line 111 and 113), using the same femur with a 40 mm bone gap.

This dual tapering reduced the structural rigidity of the proximal plate, thus partially reducing the plate's ability to resist the normal in vivo bending of the upper femoral segments during patient weight-bearing. It is useful to relate these data to the intended clinical application of leg-lengthening fixation.

In leg-lengthening, after obtaining the appropriate femoral length, the gap site is grafted with cancellous bone and then plated. If a dual taper 6/4 plate is used, FIG. 10 demonstrates that initial femoral loading, with a 40 mm gap, will subject the first three proximal screws to a bending strain range not greater than 100 $\mu\epsilon$. During the extended period of healing, the screw bending strain distribution will shift toward tensile bending, however, the three most proximal screws will not have changed their bending strains by more than 100 $\mu\epsilon$ (based on the standard 20 kg. spinal load employed). Under the same loading conditions, the three most proximal screws of the 4/4 plate are subjected to a bending strain range of 300 $\mu\epsilon$ for a 40 mm bone gap, and shift toward tensile bending, during the healing phase, to a screw bending strain level 2 to 3 times greater than that observed in the 6/4 dual taper plate. These results demonstrate that the 6/4 dual-taper plate substantially reduces the bending strains and direction encountered by the most proximal screws (positions 1 and 2 in FIG. 10), which are most prone to initial failure.

Clinical data involving gap healing indicate that the majority of proximal screw failures occur approximately within the early healing period. As a function of healing time, therefore, these screws are subjected to a greater degree of cyclic loading, and a higher chance for premature fatigue failure, than would normally be encountered during fracture repair. Clinically, the transition period between the 40 mm gap and "healed" condition appears to be the critical time during which the most proximal plate screws should ideally be at their lowest bending strain levels; subjected to the smallest possible change in strain levels with minimal changes in their bending directions. The screw strain distributions for the dual-taper 6/4 plate satisfy these three criteria when compared to the conventional prior art 4/4 leg lengthening plate.

These investigations also provided a major contribution to the understanding of generic plate fixation by identifying four unique screw stain distribution patterns. Of particular importance is the finding that plate screws do not exhibit a linear strain bending distribution when transferring loads between bone and plate, but instead vary considerably as a function of bone discontinuity, degree of osseous healing and anatomic loading conditions. Furthermore, different plate screw positions are subjected to maximum bending strains during different stages in the osseous healing process. Two additional factors, that of screw bending strain reversals and the duration of healing, also have contributed to the overall understanding of screw load transfer, be it for the design of leg-lengthening plates or for fracture plate fixation.

For example, in fracture fixation the profile of the clinical screw bending strain distribution depends directly upon achieving and maintaining adequate fracture reduction. As shown in FIG. 6 and diagrammatically in FIG. 12, if bone-to-bone contact is obtained then the proximal screws will remain in tensile bending throughout the healing period, while the distal screws will reverse their bending direction during the same period. If there is inadequate reduction, the proximal and distal screw groups will exhibit reverse bending strain distributions. Furthermore, the net change in bending strains, for both the proximal and distal screw groups, will be greater.

My invention offers a reduction in screw bending strain directions while maintaining the lowest possible bending strains in the most proximal screws. When compared to the conventional, known prior art leg-lengthening plate, my invention substantially reduces screw bending strains, which lead to the occurrence of proximal screw failure and its associated complications. In addition, positioning the plate on the lateral femoral aspect, as opposed to posterior placement, will further simplify the current surgical procedure.

The plate of the present invention was developed in response to a significant number of fixation failures occuring in patients undergoing femoral leg-lengthening. Since this reconstructive procedure necessitates the use of large-gap cancellous bone grafts, fixation failure results in several complications—potential loss of leg length; an increased risk in delay union; increased hospitalization and its associated costs; and additional surgery to re-stablize the leg-length site, which has been previously subjected to at least two surgical procedures. The plate of the present invention reduces the likelihood of fixation failure and the medical complications resulting therefrom.

Although the present invention has been described with reference to the preferred embodiments, it should be apparent to those skilled in the art that various modifications and improvements may be made in and to the reconstruction or fracture plate, without departing from the spirit and scope of the invention.

What is claimed is:

1. A reconstruction or fracture plate for bridging a discontinuity in a long bone of a patient comprising:
   a longitudinal axis for placement generally in alignment with a long axis of the long bone;
   a transversal axis perpendicular to the longitudinal axis;

a central portion for placement over the bone discontinuity;

a first end portion for abutting placement against the long bone on one side of the bond discontinuity, the first end portion having a dual-tapered width and thickness profile for decreasing plate cross section and increasing plate flexibility along the longitudinal axis away from the central portion and the first end portion defining a first plurality of screw holes for receipt of bone screws, each hole having a central axis; and a second end portion for abutting placement against the long bone on a second side of the bone discontinuity, defining a second plurality of screw holes for receipt of bone screws, each having a central axis;

the first and second plurality of screw holes each having a central axis pattern oriented relative to the plate longitudinal and transversal axes with plate taper and the distribution and orientation of the screw holes chosen to maintain bone screw bending strain direction and magnitude within limitations which reduce the likelihood of screw failure during the patient's bone healing process.

2. The reconstruction or fracture plate of claim 1, wherein the first end portion has a greater number of screw holes than the second end portion.

3. The reconstruction or fracture plate of claim 2, wherein the first end portion has six (6) screw holes and the second end portion has four (4) screw holes.

4. The reconstruction or fracture plate of claim 1, wherein the second end portion has a dual-tapered width and thickness profile for decreasing plate cross section and increasing plate flexibility along the longitudinal axis away from the central portion.

5. The reconstruction or fracture plate of claim 4, wherein the first end portion has six (6) screw holes and the second end portion has four (4) screw holes.

6. The reconstruction or fracture plate of claim 1, wherein the first plurality of screw holes have an asymmetrically oriented central axis spacing pattern relative to each other.

7. The reconstruction or fracture plate of claim 1, wherein the second plurality of screw holes have an asymmetrically oriented central axis spacing pattern relative to each other.

8. A reconstruction or fracture plate for bridging a discontinuity in a long bone of a patient comprising:

a longitudinal axis for placement generally in alignment with a long axis of the long bone;

a transversal axis perpendicular to the longitudinal axis;

a central portion for placement over the bone discontinuity;

a first end portion for abutting placement against the long bone on one side of the bone discontinuity, the first end portion having dual-tapered width and thickness profile for decreasing the plate cross section and increasing plate flexibility along the longitudinal axis away from the central portion and defining six (6) screw holes for receipt of bone screws, each hole having a central axis; and a second end portion for abutting placement against the long bone on a second side of the bone discontinuity, defining four (4) screw holes for receipt of bone screws, each having a central axis;

the screw holes on each end portion having a central axis pattern oriented relative to the plate longitudinal and transversal axes with the plate taper and the distribution and orientation of the screw holes chosen to maintain bone screw bending strain direction and magnitude within limitations which reduce the likelihood of screw failure during the patient's bone healing process.

9. A reconstruction or fracture plate for bridging a discontinuity in a long bone of a patient comprising:

a longitudinal axis for placement generally in alignment with a long axis of the long bone;

a transversal axis perpendicular to the longitudinal axis;

a central portion for placement over the bone discontinuity;

a first end portion for abutting placement against the long bone on one side of the bone discontinuity, the first end portion having dual-tapered width and thickness profile for decreasing the plate cross section and increasing plate flexibility along the longitudinal axis away from the central portion and defining six (6) screw holes for receipt of bone screws, each hole having a central axis; and a second end portion for abutting placement against the long bone on a second side of the bone discontinuity, the second end portion having dual-tapered width and thickness profile for decreasing the plate cross section and increasing plate flexibility along the longitudinal axis away from the central portion and defining four (4) screw holes for receipt of bone screws, each having a central axis;

each of the end portions having screw holes having a central axis pattern oriented relative to the plate longitudinal and transversal axes with the plate taper and the distribution and orientation of the screw holes chosen to maintain bone screw bending strain direction and magnitude within limitations which reduce the likelihood of screw failure during the patient's bone healing process.

* * * * *